(12) United States Patent
Teles et al.

(10) Patent No.: US 8,614,342 B2
(45) Date of Patent: Dec. 24, 2013

(54) PROCESS FOR PREPARING EPOXYCARBOXYLIC ESTERS

(71) Applicant: BASF SE, Ludwigshafen (DE)

(72) Inventors: Joaquim Henrique Teles, Waldsee (DE); Rainer Klopsch, Worms (DE); Bianca Seelig, Cologne (DE)

(73) Assignee: BASF SE, Ludwigshafen (SE)

( * ) Notice: Subject to any disclaimer, the term of this patent is extended or adjusted under 35 U.S.C. 154(b) by 0 days.

(21) Appl. No.: 13/751,604

(22) Filed: Jan. 28, 2013

(65) Prior Publication Data

US 2013/0197246 A1   Aug. 1, 2013

Related U.S. Application Data

(60) Provisional application No. 61/592,609, filed on Jan. 31, 2012.

(51) Int. Cl.
*C07D 301/12* (2006.01)

(52) U.S. Cl.
USPC ....................................................... 549/531

(58) Field of Classification Search
USPC ....................................................... 549/531
See application file for complete search history.

(56) References Cited

U.S. PATENT DOCUMENTS

| | | | |
|---|---|---|---|
| 5,329,024 A | 7/1994 | Jureller et al. | |
| 2003/0055293 A1* | 3/2003 | Wurziger et al. | 568/451 |

FOREIGN PATENT DOCUMENTS

| | | |
|---|---|---|
| EP | 1 489 074 A1 | 12/2004 |
| EP | 2 354 131 A1 | 8/2011 |
| WO | WO 2011/157551 A1 | 12/2011 |
| WO | WO 2012/065879 A1 | 5/2012 |

OTHER PUBLICATIONS

Albrecht Berkessel, et al., "Mn-trimethyltriazacyclononane/ascorbic acid: a remarkably efficient catalyst for the epoxidation of olefins and the oxidation of alcohols with hydrogen peroxide", Tetrahedron Letters, vol. 40, 1999, pp. 7965-7968.
Dirk E. DeVos, et al., "Epoxidation of Terminal or Electron-deficient Olefins with $H_2O_2$, catalysed by Mn-trimethyltriazacyclonane Complexes in the Presence of an Oxalate Buffer", Tetrahedron Letters, vol. 39, 1998, pp. 3221-3224.
International Search Report issued Mar. 26, 2013 in PCT/EP2013/051034 filed Jan. 21, 2013 (with English Translation of Categories of Cited Documents).
Christopher B. McPake, et al., "Epoxidation of alkenes using HOF•MeCN by a continuous flow process", Tetrahedron Letters 50, XP025989811, 2009, pp. 1674-1676.

* cited by examiner

*Primary Examiner* — Taylor Victor Oh
(74) *Attorney, Agent, or Firm* — Oblon, Spivak, McClelland, Maier & Neustadt, L.L.P.

(57) ABSTRACT

Process for preparing epoxides of the formula I where R is an organic group having from 1 to 10 carbon atoms,
by reacting compounds of the formula II with an oxidant, wherein
the preparation is carried out continuously in a tube reactor.

11 Claims, No Drawings

PROCESS FOR PREPARING EPOXYCARBOXYLIC ESTERS

The present invention relates to a process for preparing epoxides of the formula I

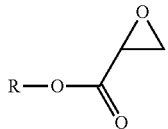

where R is an organic group having from 1 to 10 carbon atoms, by reacting compounds of the formula II

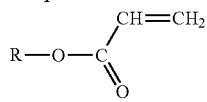

with an oxidant, wherein the preparation is carried out continuously in a tube reactor.

Epoxides have great importance for a wide variety of industrial applications and in particular also as starting materials for further chemical syntheses.

Epoxides of the formula I are, for example, starting materials for the preparation of carbonates, as described in the as yet unpublished patent applications PCT/EP2011/058945 and PCT/EP2011/069626.

There is therefore a need for very inexpensive and effective syntheses for preparing the epoxides.

Albrecht Berkessel et al, Tetrahedron Letters 40 (1999), 7965-7968 describe the preparation of epoxides of the formula I by oxidation of methyl acrylate by means of hydrogen peroxide in the presence of a manganese complex and oxalate. No information is given regarding a continuous preparation.

The use of manganese complexes and oxalates as catalysts or cocatalysts in the epoxidation of olefins by means of hydrogen peroxide is also described in Dirk E. de Vos et al, Tetrahedron Letters 39 (1998), 3221-3224.

Continuous processes for the epoxidation of olefins are mentioned in U.S. Pat. No. 5,329,024 and EP-A 2 354 131. However, EP-A 2 354 131 does not relate to the epoxidation of acrylates. U.S. Pat. No. 5,329,024 mentions acrylates in addition to other olefins as possible starting materials for epoxidation; as possible reactors for a continuous preparation, tube reactors or stirred vessels are mentioned as options.

It was an object of the present invention to provide a simple and effective process for preparing epoxides from acrylates; the epoxides should, in particular, be obtained in very high yield and selectivity.

The process defined at the outset has accordingly been found.

The starting materials epoxides of the formula I

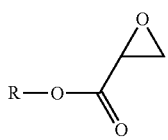

are prepared from compounds of the formula II

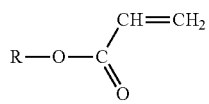

where the radical R in the two formulae is identical, by means of the process of the invention.

R is an organic group having from 1 to 10 carbon atoms. The organic group can also comprise heteroatoms, for example oxygen and nitrogen, in addition to carbon and hydrogen atoms. Oxygen and nitrogen can be present, in particular, as constituent of a hydroxyl, ether, amino or nitro group.

Preference is given to R not comprising any heteroatoms and therefore being a hydrocarbon group. The hydrocarbon group can be an aromatic or aliphatic hydrocarbon group.

In a preferred embodiment, R is a C1-C10-alkyl group. The alkyl group can be linear or branched. R is particularly preferably a C1-C4-alkyl group such as a methyl, ethyl, n-propyl, isopropyl, n-butyl or tert-butyl group.

R is very particularly preferably a methyl group.

The starting compound of the formula II is then, in the case of the above preferred embodiments, a C1-C10- or C1-C4-alkyl acrylate and very particularly preferably methyl acrylate.

The compounds of the formula I are reacted with an oxidant. Possible oxidants are conventional oxidants, e.g. peroxides or peracids. A preferred oxidant is hydrogen peroxide ($H_2O_2$). Hydrogen peroxide is preferably used in the form of an aqueous solution. The concentration of the hydrogen peroxide in water is preferably from 10 to 70% by weight, in particular from 20 to 60% by weight, based on the solution (i.e. total weight of hydrogen peroxide and water).

The oxidant, preferably hydrogen peroxide, is preferably used in a molar excess so that the starting compound of the formula I is reacted as completely as possible; the oxidant can be used in amounts of, for example, from 1.1 to 2 equivalents, in particular from 1.2 to 1.7 equivalents, based on 1 equivalent of the starting compound of the formula II.

The reaction is preferably carried out in the presence of a manganese complex as catalyst.

Possible manganese complexes are those described in Albrecht Berkessel et al, Tetrahedron Letters 40 (1999), 7965-7968, and Dirk E. de Vos et al, Tetrahedron Letters 39 (1998), 3221-3224.

Preference is given to manganese-nitrogen complexes, preferably those in which the manganese in its respective oxidation state is coordinated to three nitrogen atoms.

The starting compounds for the manganese-nitrogen complex, i.e. a manganese salt and a nitrogen compound suitable for complex formation, are preferably added to the reaction mixture. The catalytic effect then commences with the in-situ formation of the manganese-nitrogen complex. The manganese-nitrogen complex ultimately catalyzes the decomposition of hydrogen peroxide, which is associated with a change of the oxidation state of the manganese cation from III to V.

Possible manganese salts are, in particular, salts of divalent manganese, e.g. $MnSO_4$.

A nitrogen compound which is well-suited to complex formation is, for example, 1,4,7-trimethyl-1,4,7-triazacyclononane (TMTACN for short).

The manganese-nitrogen complex or the manganese salt and the nitrogen compound is/are preferably used in each case in amounts of from 0.005 to 0.2 mol, particularly preferably from 0.01 to 0.1 mol and very particularly preferably from 0.02 to 0.08 mol, per 100 mol of the starting compound of the formula II.

Apart from the catalyst, a cocatalyst is preferably also used. A suitable cocatalyst is, in particular, a reducing agent such as ascorbic acid, squaric acid, oxalic acid or an oxalate, e.g. sodium oxalate. Preference is given to oxalic acid or an oxalate. Particular preference is given to an oxalic acid/oxalate system; this acts as buffer.

The amount of cocatalyst can be, for example, from 0.1 to 20 mol, in particular from 0.5 to 10 mol and particularly preferably from 1 to 5 mol, per 100 mol of the starting compound II.

Carrying out the Process

According to the invention, the preparation of the epoxides of the formula II is carried out continuously in a tube reactor.

In the continuous preparation, the starting materials are fed continuously into the tube reactor and the product mixture formed is continuously discharged.

The above starting materials can be fed in separately; however, any of the abovementioned starting materials can also be mixed and fed as a mixture into the tube reactor.

In a preferred embodiment, two mixtures are produced beforehand:
an aqueous solution comprising the water-soluble starting materials, preferably hydrogen peroxide and oxalic acid/oxalate, and
an organic solution comprising the compound of the formula II and starting compounds soluble therein; this is preferably a solution of the manganese-nitrogen complex or the starting compounds for this in the acrylic compound of the formula II.

These two mixtures are, in the preferred embodiment, continuously taken from two stock vessels and fed to the tube reactor by means of a suitable pump system.

The reaction in the tube reactor is exothermic and commences immediately. The tube reactor is cooled so that the reaction preferably occurs at a temperature in the tube reactor of from 0 to 40° C., in particular from 0 to 30° C. The reaction can be carried out at atmospheric pressure, subatmospheric pressure or superatmospheric pressure. A small superatmospheric pressure of an inert gas, in particular nitrogen, is advantageous so as to aid bubble-free distribution, mixing and transport of the reaction medium in the tube reactor. The gauge pressure can be, for example, from 1 to 10 bar.

For the present purposes, the term tube reactor refers to the entire reactor unit; this can comprise a single tube or a plurality of tubes connected in parallel. The tubes preferably have only a small internal diameter and are therefore also referred to as capillaries.

The tube reactor preferably comprises one or more capillaries connected in parallel through which the reaction mixture flows, with the capillaries having an internal diameter of less than 5 millimeters, in particular less than 3 millimeters, in particular, an internal diameter of less than 2 millimeters or less than 1 millimeter is also possible. The internal diameter of the capillaries is generally at least 0.1 millimeter.

Very particularly preferred internal diameters of the capillaries are in the range from 0.1 to 5 millimeters, in particular from 0.2 to 4 millimeters, very particularly preferably from 0.5 to 3 millimeters.

Here, the internal diameter of the capillaries is the greatest diameter along the cross-sectional area; in the case of a circular or semicircular cross section of the capillaries, this is twice the radius.

The length of the capillaries is preferably at least 5 meters, in particular at least 10 meters. Very well-suited tube reactors have, for example, one or more capillaries having a length of from 10 to 150 meters, in particular from 20 to 130 meters and in a particularly preferred embodiment from 30 to 100 meters.

In a preferred embodiment, the tube reactor comprises at least two capillaries connected in parallel, e.g. from 2 to 5 capillaries connected in parallel, and in particular comprises two capillaries connected in parallel.

The residence time of the reaction mixture in the tube reactor or in the capillaries is preferably from 5 to 200 minutes, particularly preferably from 10 to 100 minutes, particularly preferably from 20 to 80 minutes.

Depending on the type and amount of the starting materials, a single-phase or two-phase reaction product is obtained after passage through the tube reactor. If and in so far as the epoxide obtained of the formula I is soluble in water, an aqueous phase comprising the epoxide is obtained. If the epoxide obtained is not soluble in water or more epoxide than is soluble in water is obtained, a phase which consists essentially of the epoxide is obtained in addition to the aqueous phase.

The organic phase (epoxide) can be separated off in a simple way; the epoxide obtained can be isolated from the aqueous phase by known methods, e.g. by extraction.

Finally, a purification of the epoxide obtained, e.g. of the combined amount of the epoxide separated off as organic phase and of the epoxide isolated by extraction, can also be carried out.

The process of the invention is a simple and effective continuous process for preparing epoxides from acrylates; the epoxides can be obtained in high yield and selectivity by means of this process.

EXAMPLES

Preparation of Methyl Epoxy Propionate (MEP)

MEP corresponds to the compound of the formula I in which R is a methyl radical.

TMTACN is 1,4,7-trimethyl-1,4,7-triazacyclononane.

The preparation was carried out continuously as per the description below.

Stock vessels were charged at the beginning of the experiment with a solution of methyl acrylate/TMTACN/Mn(II) acetate (stock vessel V1) and a solution of $H_2O_2$/Na oxalate/oxalic acid (stock vessel V2) and, to improve transport and avoid gas bubbles in the pump heads, blanketed with 5 bar of nitrogen. The streams 1 (methyl acrylate/TMTACN/Mn(II) acetate) and 2 (hydrogen peroxide+sodium oxalate+oxalic acid) were fed into the reactor by means of Kontron or Bischoffs pumps (controlled via the measured weight).

The reactor comprised two parallel semicircular microchannels having a radius of 1.2 mm and a total volume of 200 ml. The streams were mixed directly before the reactor, conveyed through the reactor and depressurized via a pressure regulator (20 bar) into the discharge vessel. To avoid an afterreaction, excess hydrogen peroxide was decomposed by means of saturated sodium sulfite solution in the discharge vessel.

The reaction of methyl acrylate with $H_2O_2$ was carried out using various starting concentrations of $H_2O_2$.

The essential features of the experimental procedure and of the epoxide obtained are shown below in summary for examples 1 to 3:

Example 1

20% Strength Aqueous $H_2O_2$ Solution

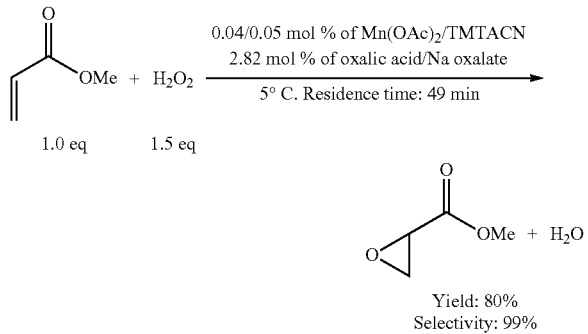

Yield: 80%
Selectivity: 99%

The mol % indicated are based on the acrylate used.
Space-time yield (STY): 244 g/liter (l)/hour (h)
The amount of TMTACN used was 1.0 g of TMTACN/kg of reaction product (MEP)

Example 2

30% Strength Aqueous $H_2O_2$ Solution

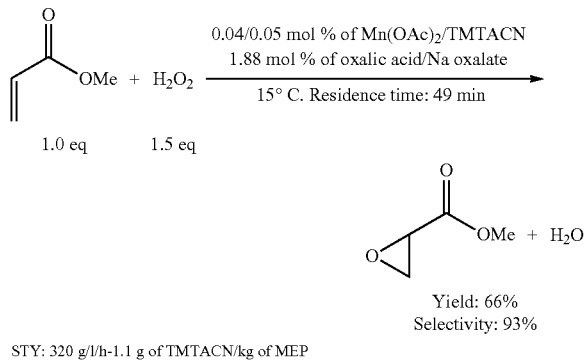

Yield: 66%
Selectivity: 93%

STY: 320 g/l/h-1.1 g of TMTACN/kg of MEP

Example 3

50% Strength Aqueous $H_2O_2$ Solution

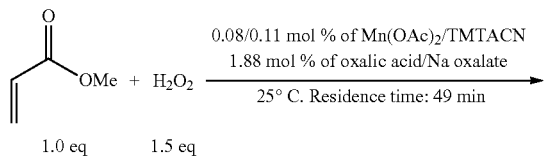

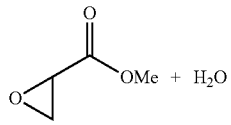

Yield: 63%
Selectivity: 86%

STY: 370 g/l/h-2.9 g of TMTACN/kg of MEP

Work-up of Examples 1 to 3

The solubility of MEP in water at 20° C. is 43 g/10 g of H2O. The density of MEP is 1.16 g/ml, i.e. above a yield of about 40% (at 50% strength $H_2O_2$), the reaction output consists of two phases, i.e. an upper aqueous phase and a lower phase composed of MEP.

For the work-up, the lower phase is separated off and MEP dissolved in the upper phase extracted. The solvent is removed under reduced pressure and the crude MEP product is distilled, going over at a temperature of 24-28° C. (10 mbar).

The essential data for the examples are summarized in the table.

| | Tmp/ °C. | $H_2O_2$/ % | TMTACN g/kg of MEP | Oxal/ mol % | Yield/ % | Selectivity/ % | STY/ g/l/h |
|---|---|---|---|---|---|---|---|
| cont. | 5 | 20 | 1.0 | 2.82 | 80 | 99 | 244 |
| | 15 | 30 | 1.1 | 1.88 | 66 | 93 | 320 |
| | 25 | 50 | 2.9 | 1.88 | 63 | 86 | 370 |

The invention claimed is:
1. A process for preparing epoxides of the formula I

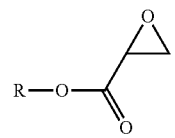

where R is an organic group having from 1 to 10 carbon atoms,
comprising reacting compounds of the formula II

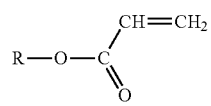

with an oxidant in the presence of 0.005 to 0.08 mol of a manganese complex as catalyst per 100 mol of compound of formula II, wherein the preparation is carried out continuously in a tube reactor.

2. The process according to claim 1, wherein R in formula I and II is a C1-C10-alkyl group.

3. The process according to claim 1 or 2, wherein the oxidant is hydrogen peroxide.

4. The process according to claim 1, wherein the reaction is additionally carried out in the presence of oxalic acid or an oxalate.

5. The process according to claim 1, wherein the tube reactor comprises one or more capillaries connected in parallel through which the reaction mixture flows, with the capillaries having an internal diameter of less than 5 millimeters.

6. The process according to claim 1, wherein the capillaries have a length of at least 10 meters.

7. The process according to claim 1, wherein the tube reactor comprises at least two capillaries connected in parallel.

8. The process according to claim 1, wherein the residence time of the reaction medium in the capillaries is from 5 to 200 minutes.

9. The process according to claim 1, wherein the reaction is carried out at a temperature of from 0 to 30° C.

10. The process according to claim 1, wherein an aqueous solution comprising the water-soluble starting materials and, separately therefrom, an organic solution comprising the compound of the formula II and starting compounds soluble thereon are fed into the tube reactor.

11. The process according to claim 10, wherein the organic solution is a solution of the manganese-nitrogen complex or starting compounds for this in the compound of the formula II.

* * * * *